United States Patent [19]

Reist-Kündig et al.

[11] 4,305,387

[45] Dec. 15, 1981

[54] DEVICE FOR PROVIDING ARTIFICIAL RESPIRATION TO PATIENTS

[75] Inventors: Francoise Reist-Kündig, Binz; Werner Vignola, Zurich, both of Switzerland

[73] Assignee: Societe Technique pour l'Industrie Nouvelle, Vevey, Switzerland

[21] Appl. No.: 169,124

[22] PCT Filed: Mar. 15, 1979

[86] PCT No.: PCT/CH79/00041

§ 371 Date: Nov. 19, 1979

§ 102(e) Date: Nov. 19, 1979

[87] PCT Pub. No.: WO79/00788

PCT Pub. Date: Oct. 18, 1979

[30] Foreign Application Priority Data

Mar. 17, 1978 [CH] Switzerland ............ 2973/78

[51] Int. Cl.³ .......................................... A61M 16/00
[52] U.S. Cl. ............................ 128/202.28; 128/207.14;
128/206.26
[58] Field of Search ............... 128/202.28, 201.18,
128/200.28, 207.14, 206.26, 206.29, 207.18,
207.15, 206.24, 136, 342

[56] References Cited

U.S. PATENT DOCUMENTS

| 1,873,160 | 8/1932 | Sturtevant | 128/207.14 |
| 2,215,126 | 9/1940 | McMillin | 128/342 X |
| 2,627,268 | 2/1953 | Leppich | 128/136 |
| 2,765,788 | 10/1956 | Raiche | 128/206.24 |
| 3,106,916 | 10/1963 | Mathes | 128/202.28 |
| 3,139,088 | 6/1964 | Galleher, Jr. | 128/206.29 |
| 3,640,282 | 2/1972 | Kamen et al. | 128/207.15 |
| 3,658,058 | 4/1972 | Neidhart et al. | 128/201.18 |
| 3,659,611 | 5/1972 | Miller | 128/207.15 |
| 3,695,264 | 10/1972 | Laveral | 128/202.28 |
| 3,730,179 | 5/1973 | Williams | 128/207.18 |
| 3,905,361 | 9/1975 | Hewson et al. | 128/202.16 |
| 3,995,643 | 12/1976 | Merav | 128/207.15 |
| 4,033,353 | 7/1977 | La Rosa | 128/207.15 |
| 4,062,357 | 12/1977 | Laerdal | 128/206.26 |

FOREIGN PATENT DOCUMENTS

| 496982 | 11/1950 | Belgium . | |
| 669841 | 1/1939 | Fed. Rep. of Germany | 128/201.18 |
| 2115715 | 2/1972 | Fed. Rep. of Germany . | |

Primary Examiner—Henry J. Recla
Attorney, Agent, or Firm—Cooper, Dunham, Clark, Griffin & Moran

[57] ABSTRACT

The mouth closure for providing artificial respiration to patients consists of a deformable elliptical plate (2), whose periphery is surrounded by a tube (1). The tube is formed in the shape of an air hose made of an elastic film with a hose (3) for admission of air. A tube (4) passes through the plate (2) in a central region. The mouth closure is placed in the dentilabial cavity of the patient's upper and lower jaws. The tube, in association with the gums and the lips and cheeks, seals the oral cavity from the outside. A flow of air through the tube therefore enters the respiratory passages of the patient and also passes back from the respiratory passages, through the tube, to the outside.

14 Claims, 5 Drawing Figures

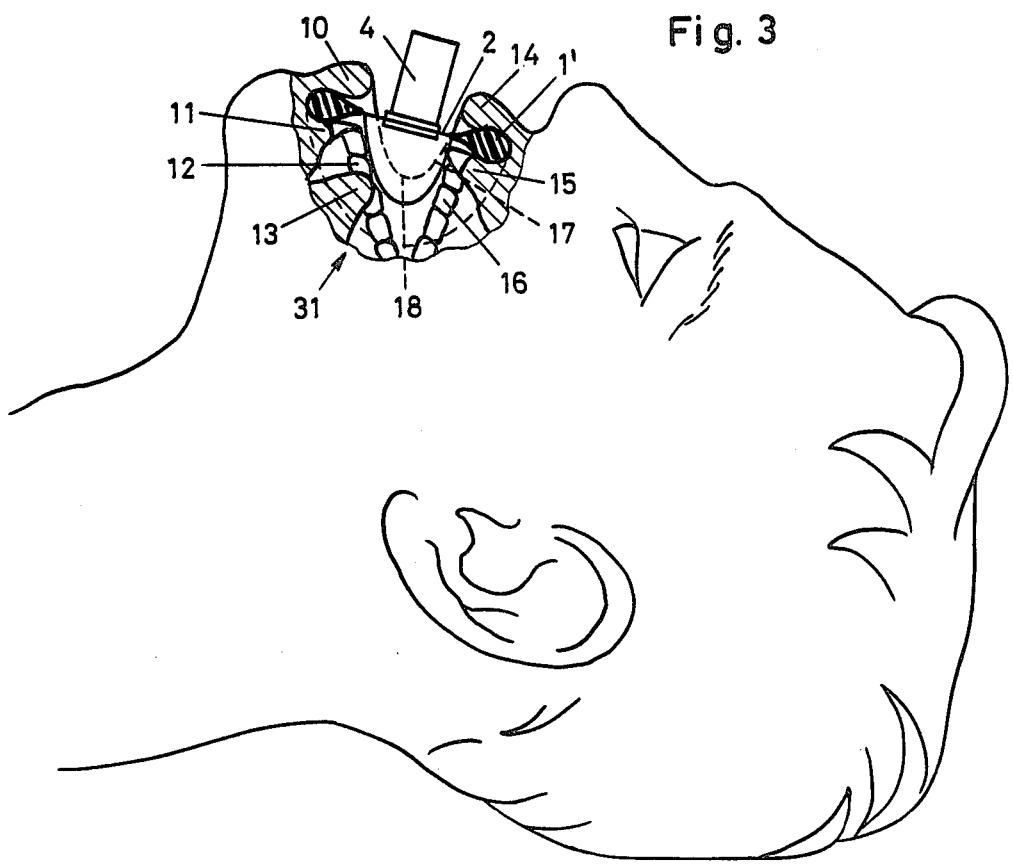
Fig. 3
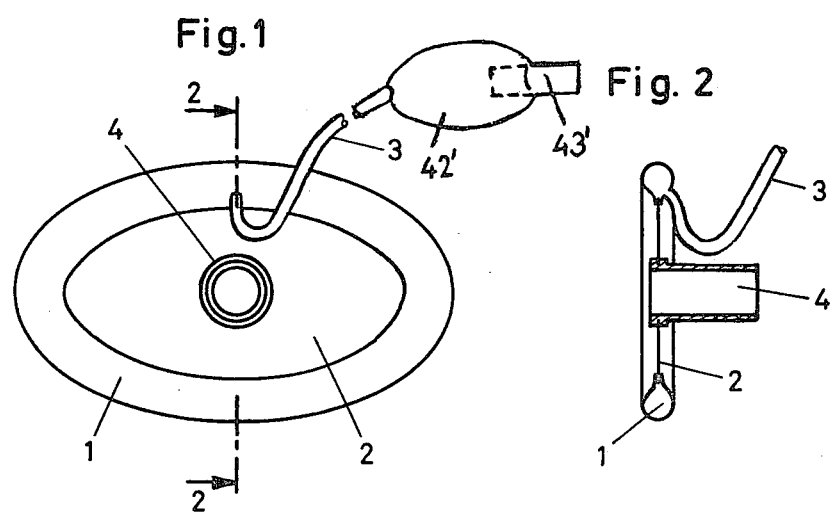
Fig. 1
Fig. 2

DEVICE FOR PROVIDING ARTIFICIAL RESPIRATION TO PATIENTS

The present invention relates to a device for providing artificial respiration to patients having a mouth closure comprising a plate and a piece of tubing passing through the latter for insertion between the gums of the upper and lower jaws on the one hand and the lips and checks on the other hand, and having a nose closure.

It has generally become known from the literature of emergency medicine that providing respiration by direct insufflation is of enormous importance, because in this way an effective respiration, which can be checked for its effectiveness without interruption, can begin instantly, and because, as is known, even a few seconds can be decisive for success in respiratory resuscitation. Therefore it is regarded as essential that each provider of first aid should master direct mouth-to-mouth insufflation, which does not involve the use of an aid. In courses on life-saving emergency measures, this is practiced assiduously on dummies. It has been found, however, that in the case of injured persons who are covered with blood and dirt, only personnel who are obligated to provide emergency help, such as professional nursing staff, policemen and firemen, are in fact able to perform this direct life-saving operation, whereas laymen, because of a psychological objection to direct contact with the patient, often cannot provide the required breath and therefore fail.

For this reason, means for avoiding direct physical contact between the provider of emergency first aid and the patient have been proposed and marketed, these means ranging from a simple mask to complicated apparatus. Furthermore, although direct insufflation is generally recommended, there are cases—involving, for example, the danger of poisoning and acute infection—wherein the necessary direct contact must be avoided on account of the risk to the assisting person. However, the permitted breathing aids must meet a large number of requirements. They must permit direct insufflation with the expired air from the assisting person without loss of time and without difficulty. Breathing aids suitable for the purpose must always permit efficient insufflation. Their use, even by unskilled helpers, should never lead to the patient's being put at any risk whatsoever.

Masks have been proposed which are fitted on the mouth and nose of the patient and are provided with a piece of tubing. However, such masks may have the effect of causing the unskilled provider of first aid to press the lower jaw downward and rearward so that the air passages at the rear wall of the pharynx are blocked by the tongue which falls backwards. Insufflation can also be rendered difficult if insufficient attention is paid to the positioning of the head for the purpose of extending the breathing passages in the region of the pharynx and neck. It has often been noticed that unskilled providers of first aid do not hold the head in the correctly supported position during manipulation for applying a mask in an air-tight manner, so that insufflation becomes impossible. In particular, in the case of masks which are pressed or tied onto the patient, there is a constant danger of aspiration with consequent stoppage of breath. Instances of death being caused by these circumstances are known.

In accordance with another proposal described, for example, in Swiss Patent Specification No. 552,988, a breathing apparatus consists of a compressible breathing pouch, a tube system with valves, and a mouthpiece. The proposed mouthpiece consists of a tube, to which is fastened a curved collar which is placed between the teeth and lips, the device also comprising a second collar which is displaceably mounted on the tube and is pressed and fixed onto the lips from the exterior by means of a clamping or retaining device. Although such a mouthpiece enables access to the oral cavity to be achieved from the outside by way of the lips and teeth, it does not fully ensure that the oral opening is sufficiently tightly sealed off on the outside to enable insufflation to take place. Furthermore, when handled by unskilled assistants, a mouthpiece of this kind presents the danger of injuries and bleeding in the oral cavity.

An object of the present invention is to provide a device which can be used by any assistant, whether skilled or unskilled, to impart breath as an aid in inducing respiration, and which does not give rise to the risk of injury to the patient.

Furthermore, the device is also intended for clinical use and in particular:

(1) for insufflation under conditions known in technical terminology as CPAP (continuous positive airway pressure), without endotracheal intubation in the case of a spontaneously breathing patient, and (2) for carrying out what the technical terminology refers to as IPPB (intermittent positive pressure breathing), during respiratory physiotherapy.

In accordance with the invention, this is achieved with a device which is described in the claims.

Embodiments of the invention will now be described in greater detail with reference to the accompanying drawings, in which:

FIG. 1 is a plan view of a mouth closure in accordance with the invention;

FIG. 2 is a section along line 2—2 in FIG. 1;

FIG. 3 is a side view, partly in section, of a human head with the mouth closure in accordance with the invention applied to it;

Figure 4:
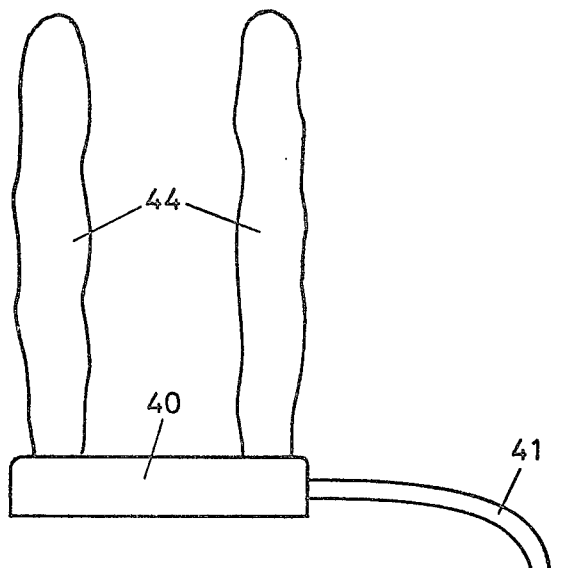
FIG. 4 is an elevation view of a nose closure device in accordance with the invention.

The mouth closure shown in FIGS. 1 and 2 comprises an inflatable tube 1 with an air-supply hose 3 leading thereto, a deformable plate 2, and a piece of tubing 4 which passes through this plate 2. The plate 2 may be made of sheet metal, for example, which can be covered on both faces with plastic film for the purpose of affording protection against corrosion, or for attaching the tube.

The tube 1 is secured to the periphery of the plate 2 and may be in the form of an inflatable ring. A hose 3 which penetrates the tube is used for inflating the tube. Inserted at the center of the plate 2 is a piece of tubing 4 which extends through the plate 2 and is connected to the plate in an air-tight manner.

Instead of an inflatable tube in accordance with the embodiment shown in FIGS. 1 and 2, a beading 1' of foamed plastic could be provided such as shown in FIG. 3. This embodiment would be particularly suitable for first-aid assistants, since no particular air pressure has to be established and monitored.

As shown in FIG. 1, the basic shape of the mouth closure is elliptical, the ellipse having a minor axis, which, in the case of a cranium of average size, terminates in the dentilabial cavity of the lower and upper jaws. The major axis of the ellipse is then so selected that the inflatable tube 1 passes across the rows of teeth behind the corners of the mouth.

As shown in FIG. 3, in a section through the mouth closure extending approximately along the line 2—2, the beading 1' rests in the dentilabial cavity of the lower jaw between the lower lip 10 and the gum 11 carrying the teeth 12, and in the dentilabial cavity of the upper jaw between the upper lip 14 and the gum 15 carrying the teeth 16. The tongue 13 is only indicated in the drawing. When the lips 10 and 14 are slightly opened, an oral opening, extending approximately along the line 17, is formed. This sectional drawing clearly shows that the beading 1' of the mouth closure moves into a position behind the corner 18 of the mouth and thus also brings about a lateral sealing of the oral cavity with respect to the outside air.

Figure 5:
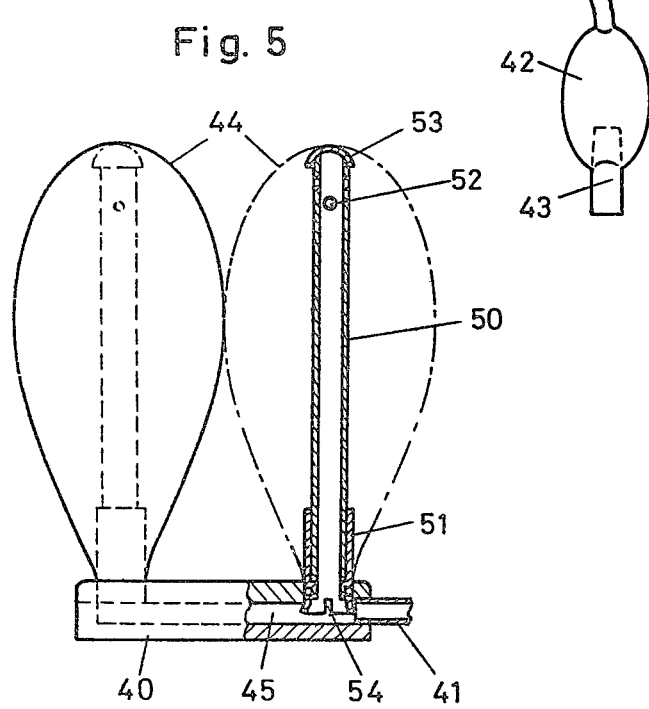
FIG. 5 is an elevation view of the nose closure device of FIG. 4 in the inflated condition and partly in section for the purpose of illustrating the construction.

The nose closure is illustrated in FIGS. 4 and 5. The FIG. 4 elevation shows two tubes 44, a support 40, an air-hose 41 including a monitoring bulb 42, and a non-return valve 43. The distance between the two tubes 44 corresponds approximately to the distance between the nostrils of an adult. The FIG. 5 sectional view shows that the support 40 has a cavity 45 into which the air-hose 41 opens.

The two tubes 44 are each secured in the support 40 in an air-tight manner by means of a tubular stem 50 and a sleeve 51. The stem 50 is provided, at its end opposite the end by which it is mounted, with a cap 53 to which the tube 44 is secured. Air is admitted to the tube 44 from the cavity 45 in the support 40, through slots 54 in the tubular stem 50 within the cavity 45 and through holes in the interior of tube 44.

Although the tubular stems 50 are shown as straight cylinders, curved tubes can also be provided. The nose closure can be used for all distances between the nostrils, particularly if the two tubes are bent towards each other. As soon as air at a definite pressure is admitted via air-hose 41 into inflatable tubes 44 which have been inserted into the nasal cavities, the inflatable tubes expand sideways. Expansion in the longitudinal direction is not possible since, as previously mentioned, the inflatable tubes 44 are secured, for example bonded, to the caps 53.

If the material of the inflatable tubes is an elastic film of natural or synthetic rubber, the tubes will move into intimate contact with the skin of the nasal cavity and will close the nose, this system being much pleasanter for the patient and less likely to cause injury than the previously used nose clips.

When the device of the invention was tried out by unskilled first-aid assistants as well as during anaesthesia in an operating theater, its great advantage over all known devices became apparent.

It was found in clinical trials that, when using CPAP (continuous positive airway pressure) on spontaneously breathing patients, endotracheal intubation is no longer necessary since the breathing passages and lungs are completely closed off from the exterior by the nose and mouth closures, and spontaneous breathing can be ensured in the same way as before by way of the tube, at a continuous excess pressure of 0.005–0.01 kg/cm$^2$. It was found that the device described permits the use of CPAP. However, it is also possible to apply PEEP (positive end-expiratory pressure) without intubation; PEEP, together with CPAP, is often used as therapy in certain forms of asthmatic syndrome. Continuous positive airway pressure (CPAP) as well as positive end-expiratory pressure (PEEP) are known to be of very considerable value in helping a patient to withdraw from the use of a respirator. During this withdrawal phase it has often been necessary, for the purpose of making effective use of positive end-expiratory pressure (PEEP), to leave the endotracheal tube in spontaneously breathing patients for quite lengthy periods in order to achieve controlled respiration. On the other hand, the mouth closure together with the proposed nose closure of the invention permits extubation at an early stage, since the respiratory measures can be instituted, interrupted or resumed at any time by simply applying the mouth and nose closures, so that the patient is able to carry out reactions such as yawning and belching, which are necessary for expanding and cleansing the lungs; this is not possible during intubation.

It is thus clear that the tube can be removed up to several days earlier, and this is extremely useful in the prophylaxis of tracheal stenosis, which is known to be extremely dangerous. Furthermore, patients suffering from acute respiratory distress syndrome (ARDS) can also be treated by continuous positive airway pressure (CPAP), thus making it possible to avoid endotracheal intubation.

Treatment under conditions of continuous positive airway pressure (CPAP) or positive end-expiratory pressure (PEEP) is indicated in the case of many functional disorders of the lung (damage or shock to the lungs following abdominal operations, multiple rib fracture, aspiration of gastric juice, or simply in the case of bed-ridden patients), which can lead to blockage of the small air passages, so that the unventilated alveoli no longer supply oxygen to the blood, and the oxygen pressure in the blood thus drops.

The mouth closure has also proven advantageous when tested as an aid in inducing respiration by insufflation, since the piece of tubing 4, which extends through the plate 2 of the mouth closure, puts a distance between the assisting person and the patient, and thus the aversion to contact with an unconscious and/or dirt-covered person is greatly reduced. No leakage, and therefore no loss of air, from the oral cavity occurred during insufflation when the mouth closure was used in this way and the nostrils were sealed manually. Because of the logical tendency of the assistant to move the mouth plate (secured by his hand and the lips of the patient) and the piece of tubing towards his mouth for the purpose of insufflation, the jaws and head of the patient are automatically brought into the extended position that is absolutely necessary for insufflation to take place.

In this case the tube 1, of course, need not be inflatable; instead, it can preferably be made of a foamed plastics material.

In the case of a tube 1 made of an elastic film of synthetic or natural rubber, a bulb 42' similar to the bulb 42 with a non-return valve 43'—as was represented in the nose closure—can be provided in the air-supply hose 3. Such a bulb enables the pressure in the tube 1 to be checked when the particular closure element is not continuously connected to a compressed air supply.

We claim:

1. Device for providing artificial respiration to patients, having a mouth closure comprising a disk means with a soft elastic edge beading and with a tube for passing gas therethrough characterized by the fact that the disk means is a flat and elastically deformable plate with an edge beading of a soft foam plastic arranged on both sides of the plate and shaped to fit in a gas-tight manner, into the dentolabial cavity of the patient to seal the oral cavity, and that the tube for passing gas projects outward from one side of, and is attached at the middle of, the plate.

2. Device for providing artificial respiration to patients, having a mouth closure comprising a disk means with a soft elastic edge beading and with a tube for passing gas therethrough, characterized by the fact that the disk means is a flat and elastically deformable plate with an edge beading in the form of a tube which can be inflated with a gas arranged on both sides of the plate and shaped to fit in a gas-tight manner, into the dentolabial cavity of the patient to seal the oral cavity, and that the tube for passing gas projects outward from one side of, and is attached at the middle of, the plate.

3. Device in accordance with claims 1 or 2, characterized by the fact that the dimensions of the plate are such that the minor axis of the ellipse is between 2 and 5 cm long, so that it can be compressed in the dentolabial cavity between the gums and the lips when the mouth is closed, and the major axis of the ellipse is between 5 and 10 cm long, so that it can be compressed between the gums and the cheeks.

4. Device in accordance with claims 1 or 2, characterized by the fact that the cross section of the beading is at least approximately circular.

5. Device in accordance with claim 4, characterized by the fact that the diameter of the circle is at least 5 mm, in order to fill the dentilabial cavity.

6. Device in accordance with claim 2, characterized by the fact that the tube is provided with a gas inlet hose which is provided with a control means for the gas pressure.

7. Device in accordance with claim 6, characterized by the fact that the control means is a bulb having flexible walls which expand in the inlet hose, and the inlet hose has a pneumatic one-way valve on the gas inlet side.

8. Device in accordance with claims 1 or 2, characterized by the fact that the gas passing tube is of suitable length to permit mouth-to-mouth resuscitation, without a direct physical contact taking place between the person providing the resuscitation and the patient.

9. Device in accordance with claims 1 or 2, characterized by the fact that the gas passing tube is in the form of a rigid tube for attachment to a breathing device.

10. Device in accordance with claim 2 provided with a nose closure and characterized by the fact that the nose closure consists of two tubes which can be inserted into the two nostrils and can be inflated with a gas under pressure, the said tubes being secured onto a support having gas lines for admitting gas under pressure, in a gas-tight manner, and a source of compressed gas external to the support for supplying gas under pressure into both of said tubes of said nose closure and into the beading tube of said mouth closure.

11. Device in accordance with claim 10, characterized by the fact that the tubes of said nose closure are made from a film of material selected from the group consisting of natural rubber, synthetic rubber, and plastic.

12. Device in accordance with claim 11, characterized by the fact that the tubes are balloon-shaped.

13. Device in accordance with claim 10, characterized by the fact that each of the tubes of said nose closure includes a tubular stem in order to assure the admittance of the compressed gas into the tubes and to facilitate the insertion of the tubes into the nasal cavities.

14. Device in accordance with claim 13, characterized by the fact that each of the tubes are secured at the end of the tubular stem, so that they can be expanded by the compressed gas only in planes perpendicular to the tubular stem, and that the tubular stem has at least one hole in a radial direction so as to provide an exit for air.

* * * * *